(12) United States Patent
Shirley et al.

(10) Patent No.: US 8,025,675 B2
(45) Date of Patent: Sep. 27, 2011

(54) TEMPORARY FILTER DEVICE

(75) Inventors: Gary B. Shirley, Bloomington, IN (US);
Bruce R. Fleck, Anthem, AZ (US);
Blayne A. Roeder, Lafayette, IN (US);
Per Hendriksen, Herlufmagle (DK)

(73) Assignee: Cook Medical Technologies LLC,
Bloomington, IN (US)

( * ) Notice: Subject to any disclaimer, the term of this patent is extended or adjusted under 35 U.S.C. 154(b) by 219 days.

(21) Appl. No.: 12/191,852

(22) Filed: Aug. 14, 2008

(65) Prior Publication Data
US 2010/0042135 A1 Feb. 18, 2010

(51) Int. Cl.
*A61B 17/00* (2006.01)
*A61F 2/06* (2006.01)
*A61F 2/82* (2006.01)

(52) U.S. Cl. ............... 606/200; 623/1.15; 623/1.12
(58) Field of Classification Search .......... 606/200, 606/108, 194, 198; 604/104–107; 623/1.11, 623/1.12
See application file for complete search history.

(56) References Cited

U.S. PATENT DOCUMENTS

| | | | | | |
|---|---|---|---|---|---|
| 5,375,612 | A | * | 12/1994 | Cottenceau et al. | 128/899 |
| 5,383,887 | A | * | 1/1995 | Nadal | 606/200 |
| 5,634,924 | A | | 6/1997 | Chevillion et al. | |
| 6,241,746 | B1 | | 6/2001 | Bosma et al. | |
| 6,267,776 | B1 | * | 7/2001 | O'Connell | 606/200 |
| 6,267,777 | B1 | * | 7/2001 | Bosma et al. | 606/200 |
| 6,350,277 | B1 | | 2/2002 | Kocur | |
| 6,409,750 | B1 | | 6/2002 | Hyodoh et al. | |
| 6,443,972 | B1 | * | 9/2002 | Bosma et al. | 606/200 |
| 6,506,205 | B2 | * | 1/2003 | Goldberg et al. | 606/200 |
| 6,582,447 | B1 | * | 6/2003 | Patel et al. | 606/200 |
| 6,881,218 | B2 | | 4/2005 | Beyer et al. | |
| 6,972,025 | B2 | * | 12/2005 | WasDyke | 606/200 |
| 7,261,731 | B2 | | 8/2007 | Patel et al. | |
| 2005/0165442 | A1 | * | 7/2005 | Thinnes et al. | 606/200 |
| 2006/0025852 | A1 | * | 2/2006 | Armstrong et al. | 623/1.17 |
| 2007/0032816 | A1 | * | 2/2007 | O'Connell et al. | 606/200 |
| 2007/0112371 | A1 | | 5/2007 | Sosnowski et al. | |
| 2008/0027481 | A1 | * | 1/2008 | Gilson et al. | 606/200 |

FOREIGN PATENT DOCUMENTS

EP 1153581 11/2001
FR 2718950 10/1995

* cited by examiner

*Primary Examiner* — Elizabeth Houston
(74) *Attorney, Agent, or Firm* — Brinks Hofer Gilson & Lione

(57) ABSTRACT

A filter device for capturing thrombi in a body vessel and transformable to a stent to maintain the blood vessel open is disclosed. The filter comprises a plurality of longitudinal struts comprising proximal and distal portions. Each proximal portion has a first end. The first ends are attached together along a longitudinal axis. Each distal portion extends from the proximal portion to an anchoring hook. The distal portions of the longitudinal struts are configured to expand in the body vessel. The device comprises a biodegradable member attached to the device for maintaining the first ends attached together in a closed position. The biodegradable member is comprised of bio-absorbable material so that the biodegradable member degrades at a predetermined time period after the filter is deployed in the body vessel allowing the first ends to radially expand to an open position defining the stent.

9 Claims, 4 Drawing Sheets

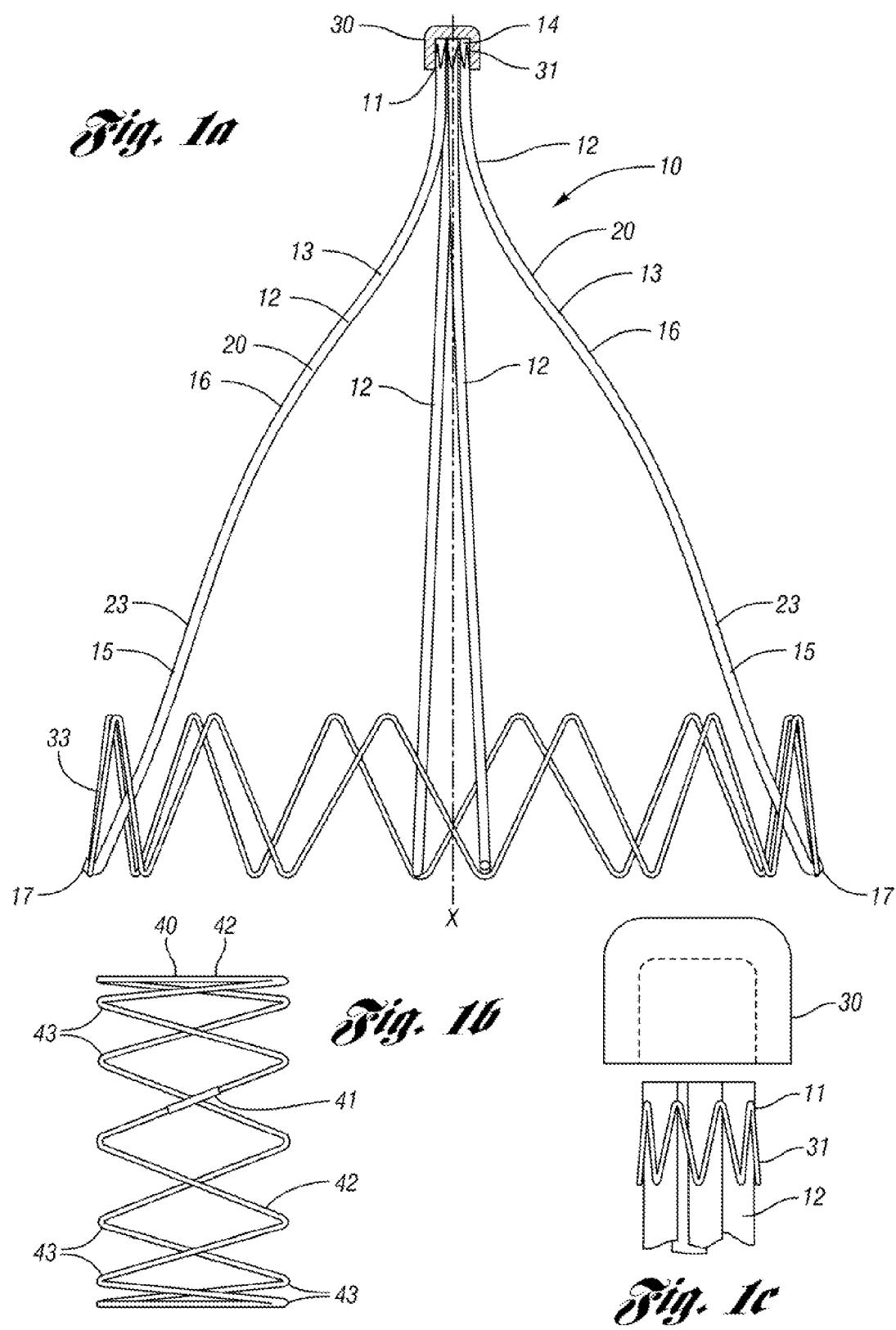

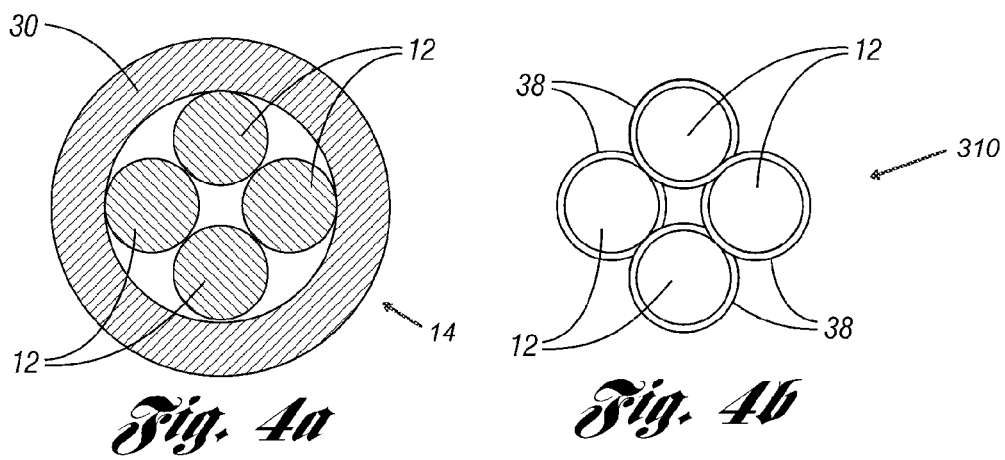
*Fig. 4a*    *Fig. 4b*
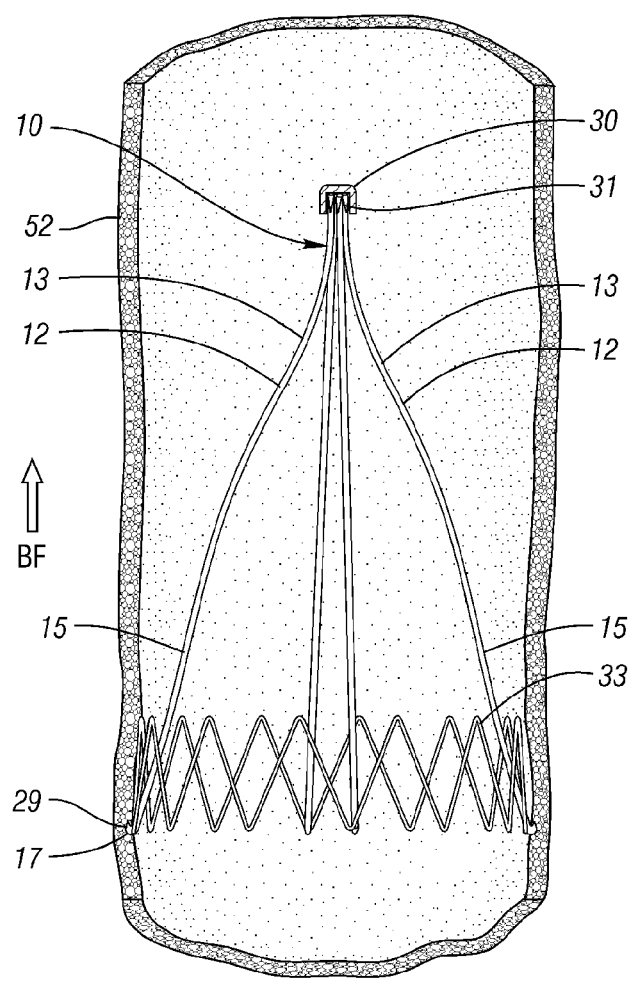
*Fig. 5a*

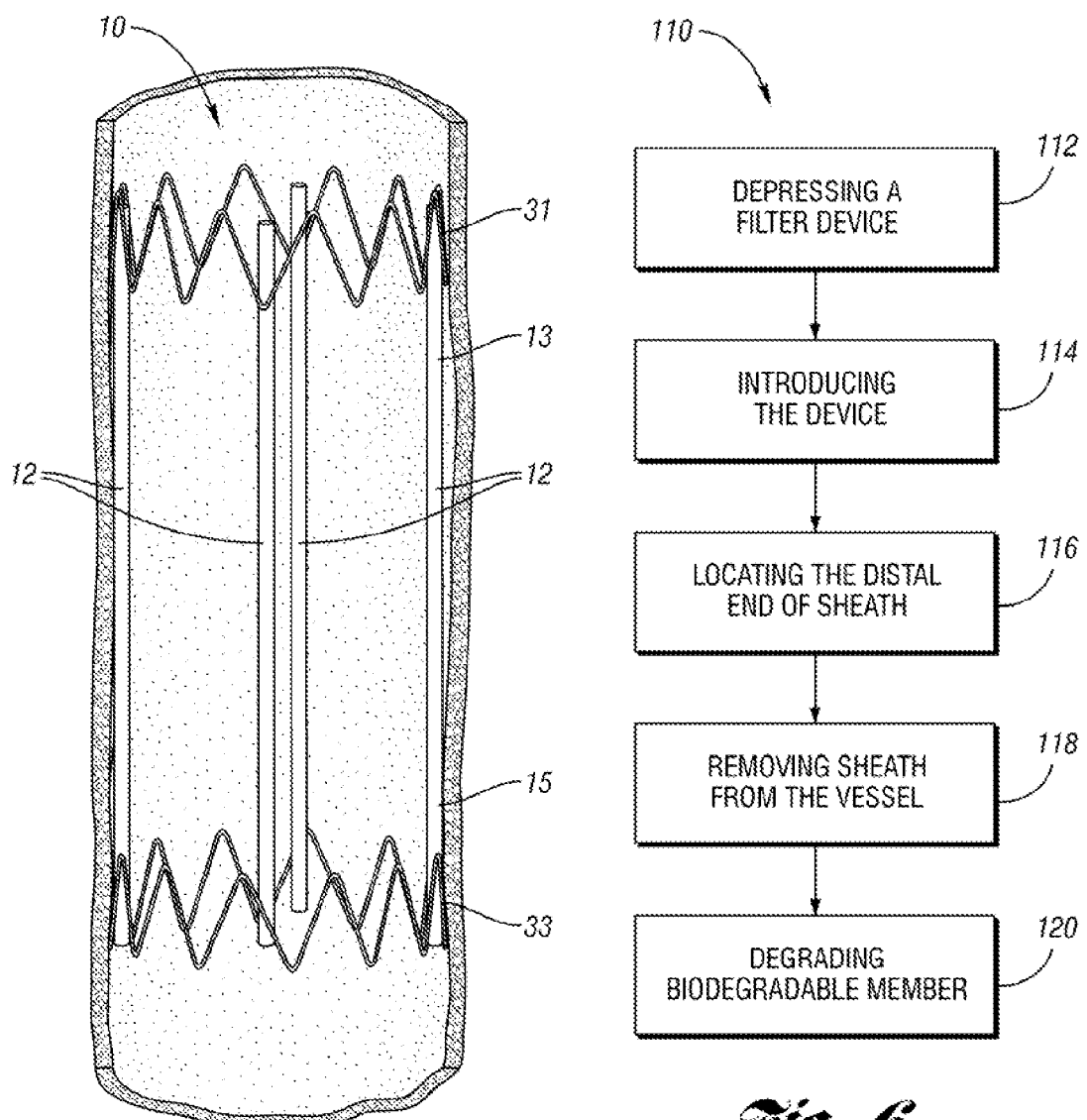

TEMPORARY FILTER DEVICE

BACKGROUND OF THE INVENTION

The present invention relates to medical devices. More particularly, the invention relates to a temporary vena cava filter that can be percutaneously placed in the vena cava of a patient and further expandable to a stent.

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

The benefits of a vena cava filter have been well established, but improvements may be made. For example, when the condition that required the filter has passed, there are situations where the body vessel is in need of a stent to maintain body vessel open or the patency thereof. Retrieval of the filter and percutaneous introduction of a stent would take additional steps to accomplish.

BRIEF SUMMARY OF THE INVENTION

The present invention provides a medical device that filters thrombi in a body vessel and, after the need for filtering passes, maintains patency in the body vessel without additional steps of percutaneous retrieval or introduction into the patient.

In one embodiment, the present invention provides a temporary filtering device for capturing thrombi in a body vessel. The device is then transformable to a stent for maintaining patency of the blood vessel. The device comprises a plurality of longitudinal struts comprising proximal and distal portions. Each proximal portion has a first end. The first ends are attached together along a longitudinal axis. Each distal portion extends from the proximal portion to an anchoring hook. The distal portions of the longitudinal struts are configured to expand in the body vessel, engaging the anchoring hooks with the body vessel.

The device further comprises first and second radial struts radially expandable and attached to the longitudinal struts. The first radial strut is disposed radially about the proximal portions to attach the first ends together. The second radial strut is disposed about the distal portions of the longitudinal struts and expandable therewith in the body vessel to engage the anchoring hooks with the body vessel. Each of the first and second radial struts is a z-wire formed into a closed zig-zag configuration including a series of straight sections and a plurality of bends. The straight sections are joined by the bends to form each of the first and second radial struts.

The device further comprises a biodegradable member attached to the first radial strut for maintaining the first ends attached together in a closed position. The biodegradable member is comprised of bio-absorbable material so that the biodegradable member degrades at a predetermined time period after the filter is deployed in the body vessel allowing the first radial strut to radially expand in an open position, defining the stent.

In one embodiment, the device is depressible into a smaller first shape wherein the straight sections are arranged side by side and closely adjacent one another for insertion into the body vessel and the bends store stress therein. The device is expandable, by the release of the stress stored in the bends of the second radial strut, into a second shape wherein straight sections press against the wall of the body vessel to engage the anchoring hooks with the body vessel. The device is expandable, by the release of the stress stored in the bends of the first radial strut when the biodegradable member degrades at the predetermined time period, into a third shape wherein straight sections press against the wall of the body vessel to maintain patency of the body vessel.

BRIEF DESCRIPTION OF THE DRAWINGS

FIG. 1a is a side elevated view of a device in a partially expanded configuration for capturing thrombi and transformable to a fully expandable configuration for maintaining patency of a body vessel in accordance with one embodiment of the present invention;

FIG. 1b is an enlarged view of a radial strut of the device in section 1b of FIG. 1a;

FIG. 1c is an exploded view of a biodegradable member of the device in FIG. 1a;

FIG. 1d is a side view of a biodegradable member of a device in accordance with another embodiment of the present invention;

FIG. 1e is a side view of a biodegradable member of a device in accordance with yet another embodiment of the present invention;

FIG. 4a is a cross-sectional view of a hub area of the device in FIG. 1a taken along line 4a-4a;

FIG. 4b is a cross-sectional view of a hub area of a device in accordance with another embodiment of the present invention;

FIG. 5a is a cross-sectional view of the vena cava in which the device of FIG. 1a has been deployed;

FIG. 5b is a cross-sectional view of the vena cava in which the device has fully expanded to the third configuration; and FIG. 6 is a flow chart of one method of capturing thrombi in a body vessel and maintaining patency of the body vessel in accordance to one example of the present invention.

DETAILED DESCRIPTION OF THE INVENTION

Figure 1B:
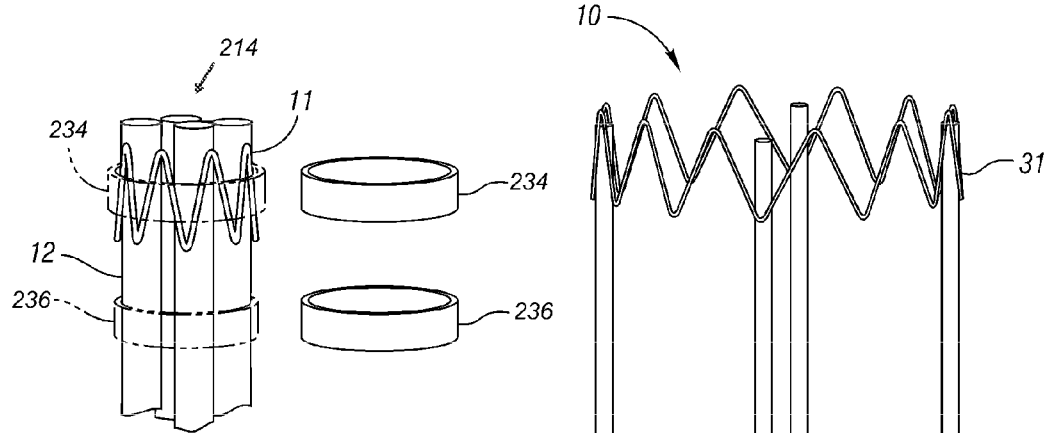

FIG. 1a depicts a device 10 for capturing thrombi in a body vessel and expandable to a stent to maintain patency of the body vessel in accordance with one embodiment of the present invention. As will be described in greater detail below, the device 10 may have a first (compressed) configuration for delivery thereof in a body vessel, a second (partially expanded) configuration for capturing thrombi in a body vessel, and a third (fully expanded) configuration for maintaining patency of the body vessel. As shown in FIG. 1a, the device 10 is in the partially expanded configuration and comprises a plurality of longitudinal struts 12 having proximal and distal portions 13,15. In this embodiment, each proximal portion 13 has a first end 14. As shown, the first ends 14 are attached together at a hub area 11 along a longitudinal axis X of the device 10. Each distal portion 15 extends from the proximal portion to an anchoring hook 17. The distal portions 15 of the longitudinal struts 12 are configured to radially expand or radially move in the body vessel, thereby engaging the anchoring hooks 17 with the body vessel. Preferably, the longitudinal struts 12 are formed from a superelastic material, stainless steel wire, Nitinol, cobalt-chromium-nickel-molybdenum-iron alloy, or cobalt chrome-alloy, or any other suitable material that will result in a self-opening or self-expanding filter and stent.

In this embodiment, the proximal and distal portions 13,15 include an arcuate segment 16 having a soft S-shape. Each arcuate segment 16 is formed with a first curved portion 20 that is configured to softly bend away from the longitudinal or central axis X of the device 10 and a second curved portion 23 that is configured to softly bend toward the longitudinal axis of the device 10. In this embodiment, the proximal portion may include the first curved portion and the distal portion may include the second curved portion. Due to the soft bends of each arcuate segment 16, a prominence or a point of inflection on the longitudinal strut 12 is substantially avoided to aid in non-traumatically engaging the vessel wall.

As previously discussed, the longitudinal struts 12 terminate at anchoring hooks 17 at the distal portion 15. In use, the anchoring hooks 17 will anchor in the vessel wall when the device 10 is deployed at a delivery location in the blood vessel. The longitudinal struts 12 are configured to move between the compressed configuration, the partially expanded configuration, and the fully expanded configuration.

When the device 10 is deployed in a blood vessel in the partially expanded configuration, the anchoring hooks 17 engage the walls of the blood vessel to define an axial portion to secure the filter in the blood vessel. The anchoring hooks 17 prevent the device 10 from migrating from the delivery location in the blood vessel where it has been deposited. The longitudinal struts 12 have sufficient spring strength that when the filter is deployed the anchoring hooks 17 will anchor into the vessel wall.

In this embodiment, the device further comprises first and second radial struts 31, 33 that are radially expandable and attached to the longitudinal struts 12. The first radial strut 31 is disposed radially about the proximal portions 13 to attach the first ends 14 together. The second radial strut 33 is disposed about the distal portions 15 of the longitudinal struts 12 and is expandable therewith in the body vessel to engage the anchoring hooks 17 with the body vessel. As shown in FIGS. 1a and 1b, each of the first and second radial struts 31, 33 is a z-wire formed into a closed zig-zag configuration including a series of straight sections and a plurality of bends. The straight sections are joined by the bends to form each of the first and second radial struts 31, 33. Of course, each of the first and second radial struts 31, 33 may be comprised a plurality of z-wires without falling beyond the scope or spirit of the present invention.

Figure 1C:
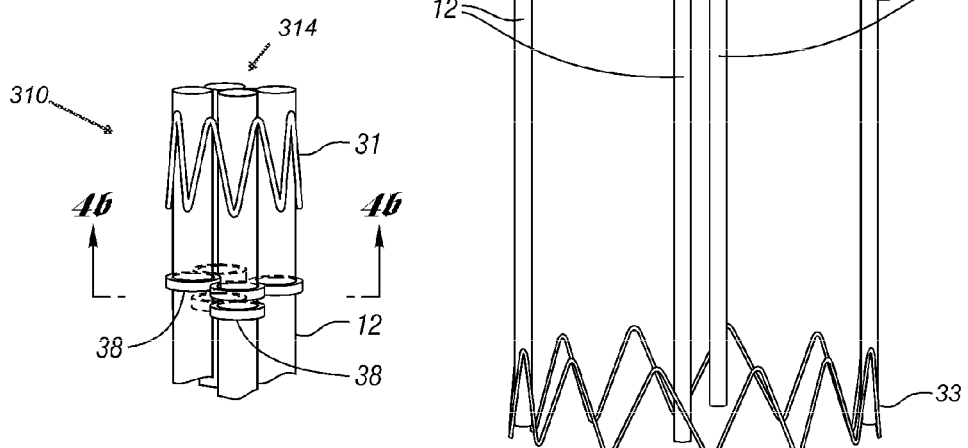

Referring now more particularly to the drawings, there is illustrated in FIG. 1b a side elevation of one of the radial struts which includes a length 40 of stainless steel wire formed in a closed zig-zag configuration. The wire is closed by a sleeve 41 which is welded to or tightly squeezed against the ends of the wire to produce the endless configuration. Referring to FIGS. 1b and 1c, the radial strut is shown in a resiliently compressed first configuration wherein the straight sections 42 are arranged side-by-side and closely adjacent one another. The straight sections 42 of the stent are joined by bends 43 which are relatively sharp.

As shown in FIGS. 1a and 1c, the device 10 further comprises a biodegradable member 30 attached to the first radial strut 31 for maintaining the first ends 14 attached together in a closed position. The biodegradable member 30 may be a biodegradable cap, a biodegradable suture wire, and a biodegradable band. In this embodiment, the biodegradable member 30 is a cap that is disposed about the first ends and covers the first radial strut 31 to contain the stress therein, preventing radial expansion of the first radial strut 31. The biodegradable member is comprised of bio-absorbable material so that the biodegradable member degrades at a predetermined time period after the filter is deployed in the body vessel. When the bio-absorbable material degrades, the hold on the first radial strut 31 in the closed position is released and the first radial strut 31 radially expands the first ends 14 in an open position, defining the fully expanded configuration (FIG. 2) which takes on the shape of a stent.

Figure 2:
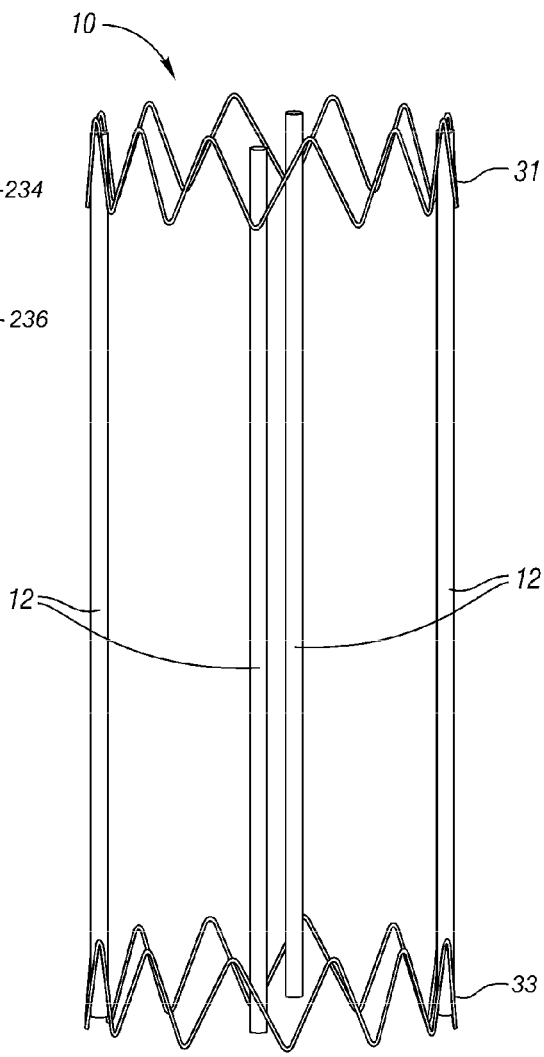
FIG. 2 is a side view of the device in the fully expanded configuration for maintaining patency of a blood vessel.

As shown in FIG. 2, the device fully expands to the third configuration defining a stent. After a predetermined time period in the body vessel, the biodegradable member degrades. Upon degradation, the hold on the first radial strut is released and the first radial strut is allowed to expand the first ends to the open position, thereby defining the fully expanded configuration. The device helps maintain patency of the body vessel.

Figure 3:
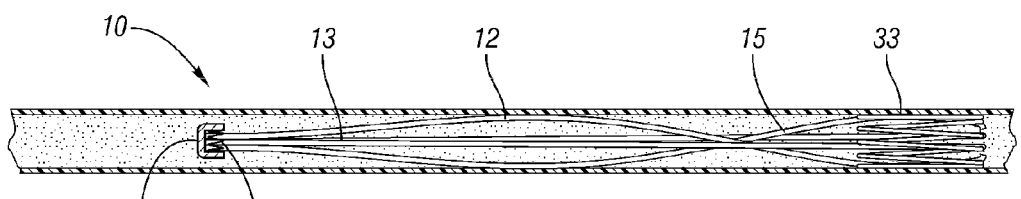
FIG. 3 is a side view of the device in a collapsed configuration.

Preferably, the device 10 is depressible into the collapsed or first configuration as shown in FIG. 3. In this embodiment, the straight sections 42 are arranged side by side and closely adjacent one another for insertion into the body vessel. In the first configuration, the bends 43 are configured to store stress. The device 10 is then partially expandable to the second configuration by the release of the stress stored in the bends 43 of the second radial strut. In the partially expanded configuration, the straight sections press against the wall of the body vessel to engage the anchoring hooks with the body vessel.

The device then expands further to the fully expanded or third configuration. More specifically, this is accomplished by the release of the stress stored in the bends of the first radial strut 31 when the biodegradable member 30 degrades at the predetermined time period. In the fully expanded configuration, the straight sections press against the wall of the body vessel to maintain patency of the body vessel.

The predetermined time period may be any suitable time period for the device to effectively filter thrombi in the body vessel. For example, the time period may be between about two to ten weeks, preferably between about three to six weeks. However, any other time period may be acceptable without falling beyond the scope or spirit of the present invention.

In another embodiment, the biodegradable member is one biodegradable band or a plurality of biodegradable bands. In one example, as shown in FIG. 1d, a first biodegradable band 234 is disposed about the first ends 214 to attach the first ends 214 together in the closed position. A second biodegradable band 236 is disposed about proximal portions 216 of the longitudinal struts 214, distally spaced apart from the first biodegradable band 234. The first biodegradable band 234 is configured to degrade at a first predetermined time period and the second biodegradable band 236 is configured to degrade at a second predetermined time period after the device is deployed in the body vessel. Preferably, the first predetermined time period is unequal to the second predetermined time period. This tailors for the bands to degrade at different timepoints and for a more gradual release of the first ends, thereby promoting an atraumatic movement of the first ends.

In this embodiment, the first and second predetermined time periods may each be any suitable time period for the device to effectively filter thrombi in the body vessel and to separately expand to the third configuration. For example, the time period may be between about two to ten weeks, preferably between about three to six weeks so long as the first predetermined time period is different than the second predetermined time period. However, any other time period may be acceptable without falling beyond the scope or spirit of the present invention.

FIGS. 1e and 4b depict a device 310 having a plurality of biodegradable suture wires 38. The suture wires 38 allow for a staggered expansion of the first ends 314 to the open position. As shown, each suture wire 38 connects at least a pair of first ends 314 together. Preferably, each suture wire 38 weaves through the longitudinal struts 12 to attach at least a pair of adjacent first ends 314 together in the closed position, since each suture wire 38 is preferably configured to degrade at different predetermined time periods. The suture wires 38 are configured for staggered degradation to allow for a staggered expansion of the longitudinal struts 12 to the open position. The biodegradable member may be made of any suitable material, such as polylactide or polyglycolide.

FIG. 3 illustrates the device 10 in the collapsed configuration disposed in a delivery tube for delivery. As shown, the device 10 is shaped for each longitudinal strut 12 to cross another longitudinal strut 12 along the longitudinal axis X. As a result, in the collapsed configuration, the anchoring hooks 17 are configured to invert or inwardly face the longitudinal axis X for delivery of the device 10.

FIG. 4a illustrates a cross-sectional view of the device 10 of FIG. 2 at hub area 11. As shown, the hub area 11 houses a bundle of first ends 14 of the four longitudinal struts 12. FIG. 5a further depicts the configurations of the longitudinal struts 12, the first radial strut, and the biodegradable member.

FIG. 6 illustrates one method 110 for capturing thrombi in a body vessel and for maintaining the body vessel open in accordance with one example of the present invention. As shown, the method comprises depressing the device 10 to the first configuration in box 112 and introducing or "loading" the device into a delivery catheter in box 114. For deployment of the device 10, the delivery tube is percutaneously inserted through the patient's vessel such that the distal end of the delivery tube is at the location of deployment. In this embodiment, a wire guide is preferably used to guide the delivery tube to the location of deployment. The method further comprises locating the distal end of the sheath in a body vessel in box 116 wherein the device in the first configuration is disposed within the distal end of the sheath. The method further comprises removing the sheath from the body vessel while holding the device in place in box 118. The stress in the second radial strut causes it to expand the distal portions of the longitudinal struts to the second configuration for engaging the anchoring hooks with the body vessel. When the device 10 is partially expanded in the vena cava, the anchoring hooks 17 of the longitudinal struts 12 are in engagement with the vessel wall. The anchoring hooks 17 of the longitudinal struts 12 have anchored the device 10 at the location of deployment in the vessel, preventing the device 10 from moving with the blood flow through the vessel. The method further comprises degrading the biodegradable member at the predetermined time period in box 120 whereby the stress in the first radial strut is released to expand the device to the third configuration to maintain the body vessel open.

FIG. 5a illustrates the device 10 partially expanded after being deployed in inferior vena cava 52. As shown, the inferior vena cava 52 has been broken away so that the device 10 can be seen. The direction of the blood flow BF is indicated in FIG. 5a by the arrow that is labeled BF. The anchoring hooks 17 at the ends of the longitudinal struts 12 are shown as being anchored in the inner lining of the inferior vena cava 52. The anchoring hooks 17 include barbs 29 that, in one embodiment, project toward the hub 11 of the filter. The barbs 29 function to retain the device 10 in the location of deployment.

The spring biased configuration of the longitudinal struts 12 further causes the anchoring hooks 17 to engage the vessel wall and anchor the device at the location of deployment. After initial deployment, the pressure of the blood flow on the device 10 contributes in maintaining the barbs 29 anchored in the inner lining of the inferior vena cava 52.

FIG. 5b illustrates the device in the fully expanded or third configuration implanted in vena cava 52. As shown, the device takes on the shape of a stent for maintaining patency of the vena cava degradation of the biodegradable member. As mentioned, the biodegradable material holds the device in the second configuration (FIG. 1) and degrades after deployment in the body vessel. Upon degradation, the device transforms or fully expands in the third configuration (FIG. 2).

While the present invention has been described in terms of preferred embodiments, it will be understood, of course, that the invention is not limited thereto since modifications may be made to those skilled in the art, particularly in light of the foregoing teachings.

What is claimed is:

1. A filter device for capturing thrombi in a body vessel and transformable to a stent to maintain the body vessel open, the filter comprising:
   a proximal end and a distal end;
   a plurality of longitudinal struts extending from the proximal end to the distal end and comprising proximal and distal portions, each proximal portion having a first end, the first ends attached together along a longitudinal axis, each distal portion extending from the proximal portion to an anchoring hook at the distal end, the distal portions of the longitudinal struts being configured to expand in the body vessel, engaging the anchoring hooks with the body vessel;
   first and second radial struts being radially expandable and attached to the longitudinal struts, the first radial strut being disposed radially about the proximal portions to attach the first ends together, the second radial strut being disposed about the distal portions of the longitudinal struts and expandable therewith in the body vessel to engage the anchoring hooks with the body vessel, each of the first and second radial struts being a z-wire formed into a closed zig-zag configuration including a series of straight sections and a plurality of bends, the straight sections being joined by the bends to form each of the first and second radial struts; and
   a biodegradable member disposed about the first ends for maintaining the first ends attached together in a closed position, the biodegradable member being comprised of bio-absorbable material so that the biodegradable member degrades after the filter is deployed in the body vessel, allowing the first radial strut to radially expand the first ends to an open position, defining the stent,
   wherein the device is depressible into a smaller first shape wherein the straight sections are arranged side by side and closely adjacent one another for insertion into the body vessel and the bends store stress therein, wherein the device is expandable, by the release of the stress stored in the bends of the second radial strut, into a second shape wherein the straight sections of the second radial strut press against the wall of the body vessel to engage the anchoring hooks with the body vessel and, wherein the device is further expandable, by the release of the stress stored in the bends of the first radial strut when the biodegradable member degrades, into a third shape wherein the straight sections of the first and second radial struts press against the wall of the body vessel to maintain the body vessel open, wherein the biodegradable member is a plurality of at least first and second biodegradable bands, the first biodegradable band being attached to the first radial strut and the second biodegradable band being disposed about the proximal portion of the longitudinal struts and distally axially spaced apart from the first biodegradable band to attach the first ends together in the closed position, the first biodegradable band being configured to degrade at a first predetermined time period and the second biodegradable band being configured to degrade at a second predetermined time period after the device is deployed in the body vessel.

2. The device of claim 1 wherein the first predetermined time period is unequal to the second predetermined time period.

3. A filter device for capturing thrombi in a body vessel and transformable to a stent to maintain the body vessel open, the filter comprising:

a proximal end and a distal end;

a plurality of longitudinal struts extending from the proximal end to the distal end and comprising proximal and distal portions, each proximal portion having a first end, the first ends attached together along a longitudinal axis, each distal portion extending from the proximal portion to an anchoring hook at the distal end, the distal portions of the longitudinal struts being configured to expand in the body vessel, engaging the anchoring hooks with the body vessel;

first and second radial struts being radially expandable and attached to the longitudinal struts, the first radial strut being disposed radially about the proximal portions to attach the first ends together, the second radial strut being disposed about the distal portions of the longitudinal struts and expandable therewith in the body vessel to engage the anchoring hooks with the body vessel, each of the first and second radial struts being a z-wire formed into a closed zig-zag configuration including a series of straight sections and a plurality of bends, the straight sections being joined by the bends to form each of the first and second radial struts; and a biodegradable member disposed about the first ends for maintaining the first ends attached together in a closed position, the biodegradable member being comprised of bio-absorbable material so that the biodegradable member degrades after the filter is deployed in the body vessel, allowing the first radial strut to radially expand the first ends to an open position, defining the stent, wherein the device is depressible into a smaller first shape wherein the straight sections are arranged side by side and closely adjacent one another for insertion into the body vessel and the bends store stress therein, wherein the device is expandable, by the release of the stress stored in the bends of the second radial strut, into a second shape wherein the straight sections of the second radial strut press against the wall of the body vessel to engage the anchoring hooks with the body vessel and, wherein the device is further expandable, by the release of the stress stored in the bends of the first radial strut when the biodegradable member degrades at the predetermined time period, into a third shape wherein the straight sections of the first and second radial struts press against the wall of the body vessel to maintain the body vessel open, wherein the biodegradable member is a plurality of biodegradable suture wires, each suture wire attaching at least a pair of adjacent first ends together in the closed position, the suture wires being configured for staggered degradation to allow for a staggered expansion of the longitudinal struts to the open position.

4. A filter device for capturing thrombi in a body vessel and transformable to a stent, the filter comprising:

a proximal end and distal end;

a plurality of longitudinal struts extending from the proximal end to the distal end and comprising proximal and distal portions, each proximal portion having a first end, the first ends attached together along a longitudinal axis, each distal portion extending from the proximal portion to an anchoring hook at the distal end, the distal portions of the longitudinal struts being configured to expand in the body vessel, engaging the anchoring hooks with the body vessel;

first and second radial struts being radially expandable and attached to the longitudinal struts, the first radial strut being disposed radially about the proximal portions to attach the first ends together, the second radial strut being disposed about the distal portions of the longitudinal struts and expandable therewith in the body vessel to engage the anchoring hooks with the body vessel, each of the first and second radial struts being a z-wire formed into a closed zig-zag configuration including a series of straight sections and a plurality of bends, the straight sections being joined by the bends to form each of the first and second radial struts; and a biodegradable member disposed about the first ends for maintaining the first ends attached together in a closed position, the biodegradable member being comprised of bio-absorbable material so that the biodegradable member degrades after the filter is deployed in the body vessel allowing the first radial strut to radially expand to an open position, defining the stent, wherein the biodegradable member is a plurality of at least first and second biodegradable bands, the first biodegradable band being attached to the first radial strut and the second biodegradable band being disposed the proximal portion of about the longitudinal struts and distally axially spaced apart from the first biodegradable band to attach the first ends together in the closed position, the first biodegradable band being configured to degrade at a first predetermined time period and the second biodegradable band being configured to degrade at a second predetermined time period after the device is deployed in the body vessel.

5. The device of claim 4 wherein the first predetermined time period is unequal to the second predetermined time period.

6. A filter device for capturing thrombi in a body vessel and transformable to a stent, the filter comprising:

a proximal end and distal end;

a plurality of longitudinal struts extending from the proximal end to the distal end and comprising proximal and distal portions, each proximal portion having a first end, the first ends attached together along a longitudinal axis, each distal portion extending from the proximal portion to an anchoring hook at the distal end, the distal portions of the longitudinal struts being configured to expand in the body vessel, engaging the anchoring hooks with the body vessel;

first and second radial struts being radially expandable and attached to the longitudinal struts, the first radial strut being disposed radially about the proximal portions to attach the first ends together, the second radial strut being disposed about the distal portions of the longitudinal struts and expandable therewith in the body vessel to engage the anchoring hooks with the body vessel, each of the first and second radial struts being a z-wire formed into a closed zig-zag configuration including a series of straight sections and a plurality of bends, the straight sections being joined by the bends to form each of the first and second radial struts; and a biodegradable member disposed about the first ends for maintaining the first ends attached together in a closed position, the biodegradable member being comprised of bio-absorbable material so that the biodegradable member degrades after the filter is deployed in the body vessel allowing the first radial strut to radially expand to an open position, defining the stent, wherein the biodegradable member is a plurality of biodegradable suture wires, each suture wire attaching at least a pair of adjacent first ends together in the closed position, the suture wires being configured for staggered degradation to allow for a staggered expansion of the longitudinal struts to the open position.

7. A method for capturing thrombi in a body vessel and for maintaining the body vessel open, the method comprising:

depressing a filter device to a first shape, the filter device comprising;

a proximal end and a distal end;

a plurality of longitudinal struts extending from the proximal end to the distal end and comprising proximal and distal portions, each proximal portion having a first end, the first ends attached together along a longitudinal axis, each distal portion extending from the proximal portion to an anchoring hook at the distal end, the distal portions of the longitudinal struts being configured to expand in the body vessel, engaging the anchoring hooks with the body vessel;

first and second radial struts being radially expandable and attached to the longitudinal struts, the first radial strut being disposed radially about the proximal portions to attach the first ends together, the second radial strut being disposed about the distal portions of the longitudinal struts and expandable therewith in the body vessel to engage the anchoring hooks with the body vessel, each of the first and second radial struts being a z-wire formed into a closed zig-zag configuration including a series of straight sections and a plurality of bends, the straight sections being joined by the bends to form each of the first and second radial struts;

a biodegradable member disposed about the first ends for maintaining the first ends attached together in a closed position, the biodegradable member being comprised of bio-absorbable material so that the biodegradable member degrades after the filter is deployed in the body vessel allowing the first radial strut to radially expand to an open position, defining the stent;

wherein the biodegradable member is a plurality of at least first and second biodegradable bands, the first biodegradable band being attached to the first radial strut and the second biodegradable band being disposed about the proximal portion of the longitudinal struts and distally axially spaced apart from the first biodegradable band being configured to degrade at a first predetermined time period and the second biodegradable band being configured to degrade at a second predetermined time period after the filter device is deployed in the body vessel;

moving the depressed device into a sheath;

locating the distal end of the sheath in a blood vessel with the device in the first shape within the distal end of the sheath;

removing the sheath from the body vessel while holding the device in place whereby the stress in the second radial strut causes it to expand the distal portions of the longitudinal struts to a second shape for engaging the anchoring hooks with the body vessel;

degrading the first biodegradable band at a first predetermined time period and degrading the second biodegradable band at a second predetermined time period whereby the stress in the first radial strut is released to expand the device to a third shape to maintain the body vessel open.

8. The method of claim 7 wherein the first predetermined time period is unequal to the second predetermined time period.

9. A method for capturing thrombi in a body vessel and for maintaining the body vessel open, the method comprising:

depressing a filter device to a first shape, the filter device comprising;

a proximal end and a distal end;

a plurality of longitudinal struts extending from the proximal end to the distal end and comprising proximal and distal portions, each proximal portion having a first end, the first ends attached together along a longitudinal axis, each distal portion extending from the proximal portion to an anchoring hook at the distal end, the distal portions of the longitudinal struts being configured to expand in the body vessel, engaging the anchoring hooks with the body vessel;

first and second radial struts being radially expandable and attached to the longitudinal struts, the first radial strut being disposed radially about the proximal portions to attach the first ends together, the second radial strut being disposed about the distal portions of the longitudinal struts and expandable therewith in the body vessel to engage the anchoring hooks with the body vessel, each of the first and second radial struts being a z-wire formed into a closed zig-zag configuration including a series of straight sections and a plurality of bends, the straight sections being joined by the bends to form each of the first and second radial struts;

a biodegradable member disposed about the first ends for maintaining the first ends attached together in a closed position, the biodegradable member being comprised of bio-absorbable material so that the biodegradable member degrades after the filter is deployed in the body vessel allowing the first radial strut to radially expand to an open position, defining the stent;

wherein the biodegradable member is a plurality of biodegradable suture wires, each suture wire attaching at least a pair of adjacent first ends together in the closed position, the suture wires being configured for staggered degradation to allow for a staggered expansion of the longitudinal struts to the open position;

moving the depressed device into a sheath;

locating the distal end of the sheath in a blood vessel with the device in the first shape within the distal end of the sheath;

removing the sheath from the body vessel while holding the device in place whereby the stress in the second radial strut causes it to expand the distal portions of the longitudinal struts to a second shape for engaging the anchoring hooks with the body vessel;

degrading the biodegradable member whereby the stress in the first radial strut is released to expand the device to a third shape to maintain the body vessel open, wherein the biodegradable member is a plurality of biodegradable suture wires, each suture wire attaching at least a pair of adjacent first ends together in the closed position, the suture wires being configured for staggered degradation to allow for a staggered expansion of the long struts to the open position.

* * * * *